United States Patent
Choi

(10) Patent No.: US 12,042,280 B2
(45) Date of Patent: Jul. 23, 2024

(54) APPARATUS AND METHOD FOR ESTIMATING OXYGEN SATURATION

(71) Applicant: SAMSUNG ELECTRONICS CO., LTD., Suwon-si (KR)

(72) Inventor: Chang Mok Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 496 days.

(21) Appl. No.: 17/377,115

(22) Filed: Jul. 15, 2021

(65) Prior Publication Data

US 2022/0233114 A1 Jul. 28, 2022

(30) Foreign Application Priority Data

Jan. 25, 2021 (KR) .................. 10-2021-0010051
Apr. 23, 2021 (KR) .................. 10-2021-0052956

(51) Int. Cl.
*A61B 5/1455* (2006.01)

(52) U.S. Cl.
CPC .. *A61B 5/14551* (2013.01); *A61B 2560/0223* (2013.01); *A61B 2562/0247* (2013.01)

(58) Field of Classification Search
CPC . A61B 5/0205; A61B 5/1455; A61B 5/14551; A61B 5/14552; A61B 5/14532; A61B 5/72; A61B 5/7221; A61B 2562/0247; A61B 2560/0223
See application file for complete search history.

(56) References Cited

U.S. PATENT DOCUMENTS

| | | | |
|---|---|---|---|
| 5,216,598 A * | 6/1993 | Branstetter | A61B 5/14551 600/330 |
| 8,265,723 B1 * | 9/2012 | McHale | A61B 5/14552 600/323 |
| 9,014,772 B2 | 4/2015 | Yamaguchi et al. | |
| 2003/0055324 A1 * | 3/2003 | Wasserman | A61B 5/0535 600/323 |
| 2006/0211925 A1 * | 9/2006 | Lamego | A61B 5/1455 600/310 |
| 2007/0078316 A1 | 4/2007 | Hoarau et al. | |
| 2010/0324384 A1 | 12/2010 | Moon et al. | |
| 2014/0114152 A1 | 4/2014 | Fournier | |
| 2016/0022181 A1 | 1/2016 | Valsan et al. | |
| 2016/0278712 A1 | 9/2016 | Sagara et al. | |
| 2017/0055846 A1 | 3/2017 | Khatam et al. | |
| 2017/0367597 A1 | 12/2017 | Fortin | |
| 2018/0132789 A1 | 5/2018 | Chen et al. | |
| 2018/0206746 A1 | 7/2018 | Narasimhan et al. | |

FOREIGN PATENT DOCUMENTS

| | | |
|---|---|---|
| JP | 2016-214731 A | 12/2016 |
| JP | 2018-161512 A | 10/2018 |
| JP | 2019-55066 A | 4/2019 |

\* cited by examiner

*Primary Examiner* — Chu Chuan Liu
(74) *Attorney, Agent, or Firm* — Sughrue Mion, PLLC

(57) ABSTRACT

An apparatus for estimating oxygen saturation is provided. The apparatus may include a sensor configured to measure optical signals of multiple wavelengths based on emitting multi-wavelength light onto an object; and a processor configured to: determine a section of the optical signals for estimating the oxygen saturation based on a difference between at least two optical signals among the optical signals of the multiple wavelengths; and estimate the oxygen saturation based on the optical signals of the multiple wavelengths in the section.

12 Claims, 12 Drawing Sheets

APPARATUS AND METHOD FOR ESTIMATING OXYGEN SATURATION

CROSS-REFERENCE TO RELATED APPLICATION(S)

This application claims priority to Korean Patent Application No. 10-2021-0010051, filed on Jan. 25, 2021, and Korean Patent Application No. 10-2021-0052956, filed on Apr. 23, 2021, in the Korean Intellectual Property Office, the disclosures of which are incorporated by reference herein in their entireties.

BACKGROUND

1. Field

The disclosure relates to oxygen saturation estimation, and more specifically, to oxygen saturation estimation using optical signals of multiple wavelengths.

2. Description of Related Art

With the aging population, increased medical costs, and a lack of medical personnel for specialized medical services, research is being actively conducted on information technology (IT)-medical convergence technologies, in which IT and medical technology are combined. Particularly, monitoring of a health condition of a human body may not be limited to places such as hospitals, but is expanded by mobile healthcare fields that may monitor a user's health condition anywhere (e.g., at home, at the office, or in transit from one place to another place) and anytime in daily life. Some examples of bio-signals, which indicate the health condition of individuals, may include an electrocardiography (ECG) signal, a photoplethysmogram (PPG) signal, an electromyography (EMG) signal, and the like, and various bio-signal sensors are being developed to measure the bio-signals in daily life.

Oxygen saturation is the fraction of oxygen-saturated hemoglobin relative to total hemoglobin (unsaturated+saturated) in the blood. The human body requires and regulates a very precise and specific balance of oxygen in the blood. Normal arterial blood oxygen saturation levels in humans are 95 to 100 percent. If the level is below 90 percent, it is considered low and called hypoxemia. Arterial blood oxygen levels below 80 percent may compromise organ function, such as functions of the brain and heart, and continued low oxygen levels may lead to respiratory or cardiac arrest. In medicine, oxygen saturation measures the percentage of hemoglobin binding sites in the bloodstream occupied by oxygen. At low partial pressures of oxygen, most hemoglobin is deoxygenated, and at around 90 percent, oxygen saturation increases according to an oxygen-hemoglobin dissociation curve. A pulse oximeter relies on the light absorption characteristics of saturated hemoglobin to provide an indication of oxygen saturation.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, an apparatus for estimating oxygen saturation may include a sensor configured to measure optical signals of multiple wavelengths based on emitting multi-wavelength light onto an object; and a processor configured to: determine a section of the optical signals for estimating the oxygen saturation based on a difference between at least two optical signals among the optical signals of the multiple wavelengths; and estimate the oxygen saturation based on the optical signals of the multiple wavelengths in the section.

The multi-wavelength light may include a first wavelength, a second wavelength that is longer than the first wavelength, and a third wavelength that is longer than the second wavelength. The processor may determine the section of the optical signals for estimating the oxygen saturation based on the difference between a first optical signal of the first wavelength and a second optical signal of the second wavelength. The processor may determine the section of the optical signals for estimating the oxygen saturation based on the difference between the first optical signal of the first wavelength and a third optical signal of the third wavelength.

The processor may determine the section based on the difference being greater than or equal to a threshold.

The processor may be further configured to provide information that requests a user to measure additional optical signals of the multiple wavelengths based on there being no section in which the difference is greater than or equal to a threshold.

The first wavelength may be less than 640 nanometers.

The sensor may include a force sensor configured to measure a force between the object and the force sensor when the object is in contact with the force sensor, and the processor may be further configured to determine the section for estimating the oxygen saturation based on a value of the force measured by the force sensor.

The processor may be further configured to determine a section in which the value of the measured force is within a threshold range as the section for estimating the oxygen saturation.

The processor may be further configured to, based on there being no section in which the value of the measured force is within the threshold range, provide information that requests a user to measure additional optical signals of multiple wavelengths, or provide information that guides the user to apply the force within a reference range.

The processor may perform calibration to preset a threshold range of the force for a user.

The processor may acquire a first feature value of the second optical signal of the second wavelength and a second feature value of the third optical signal of the third wavelength in the section, and estimate the oxygen saturation based on the first feature value and the second feature value.

The processor may acquire the first feature value and the second feature value based on a point in time at which the second optical signal of the second wavelength or the third optical signal of the third wavelength includes a maximum amplitude in the section or a median point in time of the section, or is further configured to acquire the first feature value and the second feature value based on statistical values of the second optical signal of the second wavelength and the third optical signal of the third wavelength in the section.

According to an aspect of an example embodiment, a method of estimating oxygen saturation may include measuring optical signals of multiple wavelengths by emitting multi-wavelength light onto an object; determining a difference between at least two optical signals among the optical signals of the multiple wavelengths; determining a section of the optical signals for estimating the oxygen saturation based on the difference between the at least two optical signals; and estimating the oxygen saturation based on the optical signals of the multiple wavelengths in the section.

The measuring of the optical signals of the multiple wavelengths may include measuring a first optical signal of a first wavelength, a second optical signal of a second wavelength that is longer than the first wavelength, and a third optical signal of a third wavelength that is longer than the second wavelength. The determining of the difference may include calculating the difference between the first optical signal of the first wavelength and the second optical signal of the second wavelength or the difference between the first optical signal of the first wavelength and the third optical signal of the third wavelength.

The determining the section may include determining the section in which the difference is greater than or equal to a threshold.

The method may include requesting a user to measure additional optical signals of the multiple wavelengths based on there being no section in which the difference is greater than or equal to a threshold.

The method may include measuring a force between the object and a sensor when the object is in contact with the sensor, and the determining the section for estimating the oxygen saturation may include determining the section based on a value of the measured force.

The determining the section for estimating the oxygen saturation may include determining a section in which the value of the measured force is within a threshold range as the section for estimating the oxygen saturation.

The method may further include guiding a user to apply force within a reference range based on there being no section in which the value of the measured force is within the threshold range.

According to an aspect of an example embodiment, an apparatus for estimating oxygen saturation may include a sensor configured to measure optical signals of multiple wavelengths by emitting multi-wavelength light onto an object; and a processor configured to: determine a point in time at which an optical signal having a longest wavelength among the optical signals of the multiple wavelengths has a maximum amplitude based on a measurement time period of measuring the optical signals of the multiple wavelengths being longer than or equal to a predetermined time period, and estimate the oxygen saturation based on the optical signals of the multiple wavelengths at the point in time.

The processor may provide information that guides a user to measure the optical signals of multiple wavelengths for at least the predetermined time period based on the sensor measuring the optical signals of the multiple wavelengths.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
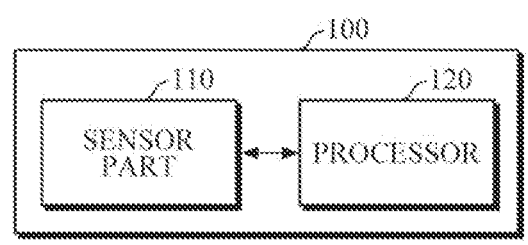
FIG. 1 is a block diagram illustrating an apparatus for estimating oxygen saturation according to an example embodiment.

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the present disclosure to those skilled in the art, and the disclosure will only be defined by the appended claims. Like reference numerals refer to like elements throughout the specification.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

It will be understood that, although the terms "first," "second," etc., may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the term "comprise," and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Hereinafter, example embodiments of an apparatus and method for estimating oxygen saturation will be described in detail with reference to the drawings.

FIG. 1 is a block diagram illustrating an apparatus for estimating oxygen saturation according to an example embodiment.

Various example embodiments of the apparatus 100 for estimating oxygen saturation may be mounted in various terminals, such as a smartphone, a tablet personal computer (PC), a desktop PC, a notebook PC, a wearable device, and the like. Here, the wearable device may include a watch type, a wristlet type, a wrist band type, a ring type, a glasses type, and a hair band type. However, the present disclosure is not limited thereto and the apparatus 100 may be mounted in hardware manufactured in various forms to be used in specialized medical institutions.

Referring to FIG. 1, the apparatus 100 for estimating oxygen saturation includes a sensor part (or sensor) 110 and a processor 120.

The sensor part 110 may measure optical signals of multiple wavelengths including a PPG signal by emitting multi-wavelength light to an object of a user.

In this case, the object may be a region of a wrist surface adjacent to the radial artery, which is an upper area of the wrist where the capillary blood or venous blood passes through, or a body part with a high blood vessel density such as a finger, a toe, an earlobe, etc.

The sensor part 110 may include a light source configured to emit light of multiple wavelengths onto the object and a detector configured to measure a PPG signal by detecting light emitted onto the object and scattered or reflected from a body tissue of the object. In this case, the light source may include at least one of a light emitting diode (LED), a laser diode, or a phosphor, but is not limited thereto. The detector may include a photodiode, a photo transistor, a photodiode array, a photo transistor array, an image sensor (e.g., complementary metal oxide semiconductor (CMOS) image sensor), etc.

An electrical, mechanical, or wired/wireless connection between the processor 120 and the sensor part 110 may be established depending on the sensor part 110. Based on receiving a request for estimating oxygen saturation, the processor 120 may control the sensor part 110 and receive optical signals of multiple wavelengths from the sensor part 110.

Based on receiving the optical signals of multiple wavelengths, the processor 120 may perform preprocessing on the received optical signals, such as filtering for noise removal, amplification of the optical signals of multiple wavelengths, conversion into digital signals, or the like. For example, the processor 120 may use a bandpass filter to perform bandpass filtering of 0.4 Hz to 10 Hz, thereby removing noise from the optical signals of multiple wavelengths received from the sensor part 110. In addition, the processor 120 may correct the optical signals of multiple wavelengths through reconstruction of the optical signals of multiple wavelengths based on fast Fourier transform. However, the present disclosure is not limited thereto, and various other preprocessing operations may be performed according to various measurement environments, such as the computing performance or measurement accuracy of the apparatus, the purpose of oxygen saturation estimation, the measurement part of the user, the temperature and humidity of the object, the temperature of the sensor part, etc.

The processor 120 may estimate oxygen saturation based on the received optical signals of multiple wavelengths. In this case, multiple wavelengths of light may include a first wavelength that is a shortest wavelength, a second wavelength that is relatively longer than the first wavelength, and a third wavelength that is relatively longer than the second wavelength. Here, the first wavelength that is the shortest wavelength may be less than 640 nanometers, but is not limited thereto.

The processor 120 may determine a suitable section for estimating oxygen saturation based on a difference between at least two optical signals among the measured optical signals of multiple wavelengths. In this case, the processor 120 may obtain normalized signals by normalizing the optical signals of multiple wavelengths and determine a suitable section for estimating oxygen saturation based on the obtained normalized signals. For example, the normalized signal may be a signal obtained by dividing an alternating current (AC) component of the optical signal of each wavelength by a direct current (DC) component of the optical signal, but is not limited thereto. Equations 1 to 3 below represent a process in which normalized signals S1, S2, and S3 are obtained by dividing an AC component of an optical signal of each wavelength by a DC component of the optical signal.

$S_1$ represents a normalized signal obtained by dividing an AC component $AC_1$ of an optical signal of the first wavelength by a DC component $DC_1$ of the optical signal, $S_2$ represents a normalized signal obtained by dividing an AC component $AC_2$ of an optical signal of the second wavelength by a DC component $DC_2$, and $S_3$ represents a normalized signal obtained by dividing an AC component $AC_3$ of an optical signal of the third wavelength by a DC component $DC_3$.

$$S_1 = AC_1/DC_1 \qquad (1)$$

$$S_2 = AC_2/DC_2 \qquad (2)$$

$$S_3 = AC_3/DC_3 \qquad (3)$$

The processor 120 may determine a suitable section for estimating oxygen saturation based on a difference between the optical signal of the first wavelength and the optical signal of the second wavelength, or a difference between the optical signal of the first wavelength and the optical signal of the third wavelength.

In this case, the optical signals of each wavelength may refer to the normalized signals $S_1$, $S_2$, and $S_3$. For example, the processor 120 may determine that a section in which the difference between the optical signal of the first wavelength and the optical signal of the second wavelength, or the difference between the optical signal of the first wavelength and the optical signal of the third wavelength, is greater than or equal to a threshold is a suitable section for estimating oxygen saturation. In addition, the processor 120 may perform a calibration to preset a threshold of the difference between the optical signal of the first wavelength and the optical signal of the second wavelength or the difference between the optical signal of the first wavelength and the optical signal of the third wavelength in consideration of the user's characteristics. Moreover, the processor 120 may request the user to re-measure the optical signals of multiple wavelengths when there is no section in which the difference is greater than or equal to the threshold.

Further, when a measurement time period of the optical signals of multiple wavelengths is longer than or equal to a predetermined time period, the processor 120 may determine that a point at which the optical signal of the longest wavelength among the optical signals of multiple wavelengths reaches the maximum amplitude is a point in time of estimating oxygen saturation, without having to determine the suitable section as described above. In this case, a threshold of the predetermined length of time may be preset for each user.

The processor 120 may estimate oxygen saturation based on the optical signals of multiple wavelengths in the determined suitable section. In this case, the processor 120 may acquire a first feature value feat$_s$ of the optical signal of the second wavelength and a second feature value feat$_2$ of the optical signal of the third wavelength at one point in time in the determined suitable section, based on the normalized signals $S_1$, $S_2$, and $S_3$ of the measured optical signals of multiple wavelengths. The processor 120 may acquire the intensities of the normalized signals $S_1$ and $S_3$ at one point in time in the determined suitable section as the first feature value $feat_1$ and the second feature value $feat_2$, respectively.

In this case, the processor 120 may acquire the first feature value $feat_1$ and the second feature value $feat_2$ based on an arbitrary point in time in the determined suitable section, a point in time at which the normalized signal $S_2$ or $S_3$ of the optical signal of the second wavelength or the third wavelength signal reaches the maximum amplitude, or a median point in time of the determined suitable section. However, the present disclosure is not limited thereto, and the first feature value $feat_1$ and the second feature value $feat_2$ may be acquired based on statistical values of the optical signal of the second wavelength and the optical signal of the third wavelength in the determined suitable section. In this case, the statistical values may include an average or median value of the intensities of the optical signals in the suitable section.

In addition, the processor 120 may estimate oxygen saturation based on the acquired first and second feature values $feat_1$ and $feat_2$. Equation 3 below shows how to obtain a ratio R of the first feature value $feat_1$ of the optical signal of the second wavelength and the second feature value $feat_2$ of the optical signal of the third wavelength. Equation 4 below illustrates how to obtain oxygen saturation $SpO_2$ through the obtained ratio R value.

$$R = \frac{feat_1}{feat_2} \quad (4)$$

$$SpO_2 = 110 - 25 \times R \quad (5)$$

Figure 2:
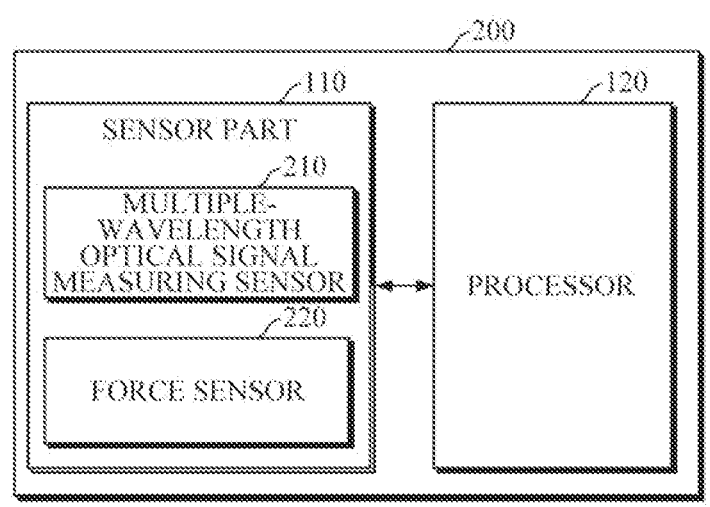
FIG. 2 is a block diagram illustrating an apparatus for estimating oxygen saturation according to another example embodiment.

FIG. 2 is a block diagram illustrating an apparatus for estimating oxygen saturation according to another example embodiment.

Referring to FIG. 2, the apparatus 200 for estimating oxygen saturation includes a sensor part 110 and a processor 120.

As illustrated, the sensor part 110 may include a multiple-wavelength optical signal measuring sensor 210 and a force sensor 220.

The multiple-wavelength optical signal measuring sensor 210 may be in contact with the object and measure a multi-wavelength optical signal from the object as described above.

The force sensor 220 may measure a force acting between the object and the force sensor 220 when the object in contact with the force sensor 220 changes the force. The force sensor 220 may include a pressure sensor, a combination of a pressure sensor and a contact area sensor, a pressure sensor array, or the like, but is not limited thereto.

When the force sensor 220 of the sensor part 110 measures the force, the processor 120 may generate information for guiding an actual force acting on the force sensor 220 by the object. In this case, the guide information may include information to induce the user to gradually increase the force applied by the object while in contact with the force sensor 220, or conversely, to induce the user to gradually decrease the force when the user initially applies the force that is greater than or equal to a predetermined threshold.

Based on receiving a request for estimating oxygen saturation from the user or an external device, the processor 120 may guide the user to bring the object into contact with the sensor part 110, and when the object is in contact with the sensor part 110, the processor 120 may guide changes in force applied by the object to the sensor part 110 during the measurement time. For example, the processor 120 may induce the user to gradually increase the force applied by the object while in contact with the sensor part 110, or induce the user to gradually decrease the force when the user presses the sensor part 110 with a force greater than or equal to a predetermined threshold. The processor 120 may provide the user with guide information related to a force between the object and the sensor part by using, for example, a display module and/or an audio output module mounted in the apparatus 100 for estimating oxygen saturation or a display module and/or an audio output module of an external device connected to the apparatus 100.

The processor 120 may determine a suitable section for estimating the oxygen saturation further based on the force value measured by the force sensor 220.

If the force acting between the object and the sensor part is too low, external light is injected into the multiple-wavelength optical signal measuring sensor 210, and venous oxygen saturation affects oxygen saturation to be measured, and thus it is not suitable for estimating the user's oxygen saturation. If the force acting between the object and the sensor part is too large, the blood vessel will be occluded, which makes it difficult to accurately measure the motion of the pulse wave.

For example, the processor 120 may determine that a section in which the difference between the optical signal of the first wavelength and the optical signal of the second wavelength, or the difference between the optical signal of the first wavelength and the optical signal of the third wavelength, is greater than a threshold and the force value measured by the force sensor 220 falls within a threshold range is a suitable section.

In addition, when there is no section in which the force value between the object and the sensor part 110 falls within the threshold range, the processor 120 may request the user to re-measure the optical signals of multiple wavelengths or guide the user to apply the force within a reference range.

In addition, since an appropriate force section may be different for each user according to the blood pressure, the location of blood vessels, and the mechanical and optical properties of the skin, the processor 120 may perform calibration to pre-set the threshold range of the force for each user for determining the suitable section for estimating oxygen saturation.

In this case, the processor 120 may obtain force values at predetermined points in time before and after the point at which the optical signal of the second wavelength or third wavelength measured by the multiple-wavelength optical signal measuring sensor 210 reaches the maximum amplitude, and may set the obtained force values as the minimum and maximum values of the threshold range of the force for determining the suitable section for estimating oxygen saturation.

Figure 3:
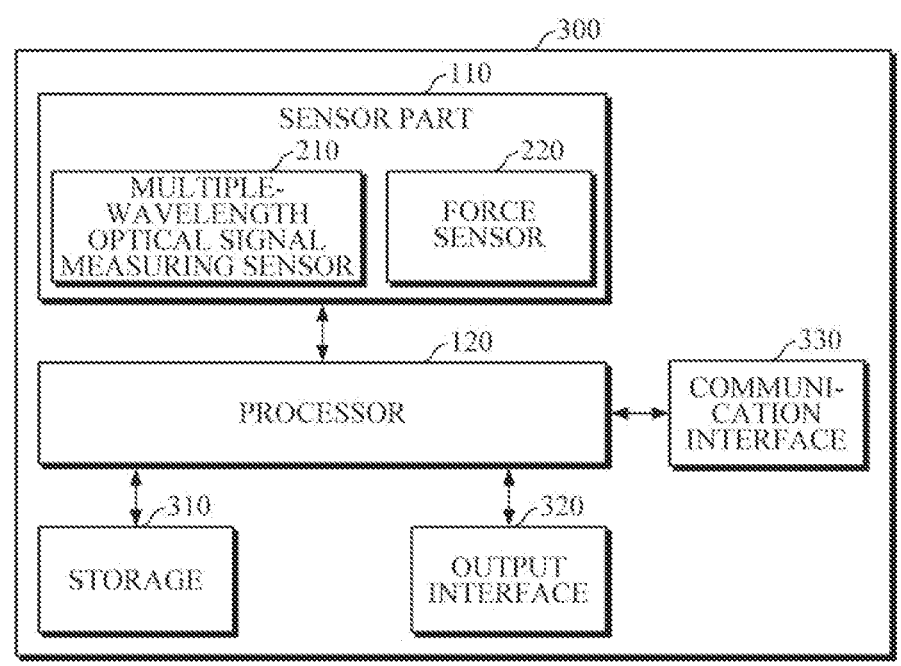
FIG. 3 is a block diagram illustrating an apparatus for estimating oxygen saturation according to still another example embodiment.

FIG. 3 is a block diagram illustrating an apparatus for estimating oxygen saturation according to another example embodiment.

Referring to FIG. 3, the apparatus 300 for estimating oxygen saturation may include a sensor part 110, a processor 120, a storage 310, an output interface 320, and a communication interface 330.

The sensor part 110 may include a multiple-wavelength optical signal measuring sensor 210 and a force sensor 220 as illustrated, but is not limited thereto and the force sensor 220 may be omitted as described with reference to FIG. 1. Hereinafter, since the sensor part 110 and the processor 120 are described above, description will be made with focus on the storage 310, the output interface 320, and the communication interface 330.

The storage 310 may store various criteria for estimating oxygen saturation, the obtained multi-wavelength optical signal, an estimated oxygen saturation value, a threshold range of force set for each user, and the like. The criteria may include user information, such as a user's age, gender, occupation, health condition, and the like, and information regarding a relationship between the optical signals of multiple wavelengths and oxygen saturation, etc., but is not limited thereto. The storage 310 may include at least one storage medium of a flash memory type memory, a hard disk type memory, a multimedia card micro type memory, a card type memory (e.g., a secure digital (SD) memory, an extreme digital (XD) memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like, but is not limited thereto.

The output interface 320 may provide the user with the optical signals of multiple wavelengths measured by the sensor part 110 and processing results of the processor 120. The output interface 320 may provide the information to the user in various visual/non-visual manners using a display module, a speaker, and a haptic device mounted in the apparatus 300.

In this case, a display area may be divided into two or more areas, wherein the optical signals of multiple wavelengths, the force between the object and the sensor part, and the like, may be output in various forms of graphs in a first area and the estimated oxygen saturation value may be output in a second area. In this case, if the estimated oxygen saturation value is not within a normal range, the output interface 320 may output warning information in various manners, such as highlighting an abnormal value in red, and the like, displaying the abnormal value along with a normal range, outputting a voice warning message, adjusting a vibration intensity, and the like.

Also, the output interface 320 may output contact pressure guide information generated by the processor 120 and a measured actual force between the object of the user and the sensor part 110 which is obtained from the force sensor 220. For example, the output interface 320 may visually output the information by using a display module, or may output the information in a non-visual manner through voice, vibrations, tactile sensation, or the like, by using a speaker module, a haptic module, or the like. For example, the output interface 320 may visually display information on a reference range of force to be applied by the user during the measurement time and/or the actual force measured by the force sensor 220.

The communication interface 330 may be connected to the external device through communication techniques under the control of the processor 120 and may receive a multi-wavelength optical signal from the external device. In this case, the external device may include, without limitation, various devices, such as smartphones, tablet PCs, wearable devices, and the like, which measure a multi-wavelength optical signal directly from the user or manage the measured multi-wavelength optical signal. Also, the communication interface 330 may transmit the processing results of the processor 120 to the external device.

In this case, the communication techniques may include Bluetooth communication, Bluetooth Low Energy (BLE) communication, near field communication (NFC), wireless local area network (WLAN) communication, ZigBee communication, infrared data association (IrDA) communication, wireless fidelity (Wi-Fi) direct (WFD) communication, ultra wideband (UWB) communication, Ant+communication, Wi-Fi communication, and mobile communication techniques, but are not limited thereto.

FIGS. 4A to 4D are diagrams for explaining a specific process of determining a suitable section for estimating oxygen saturation.

Figure 4A:
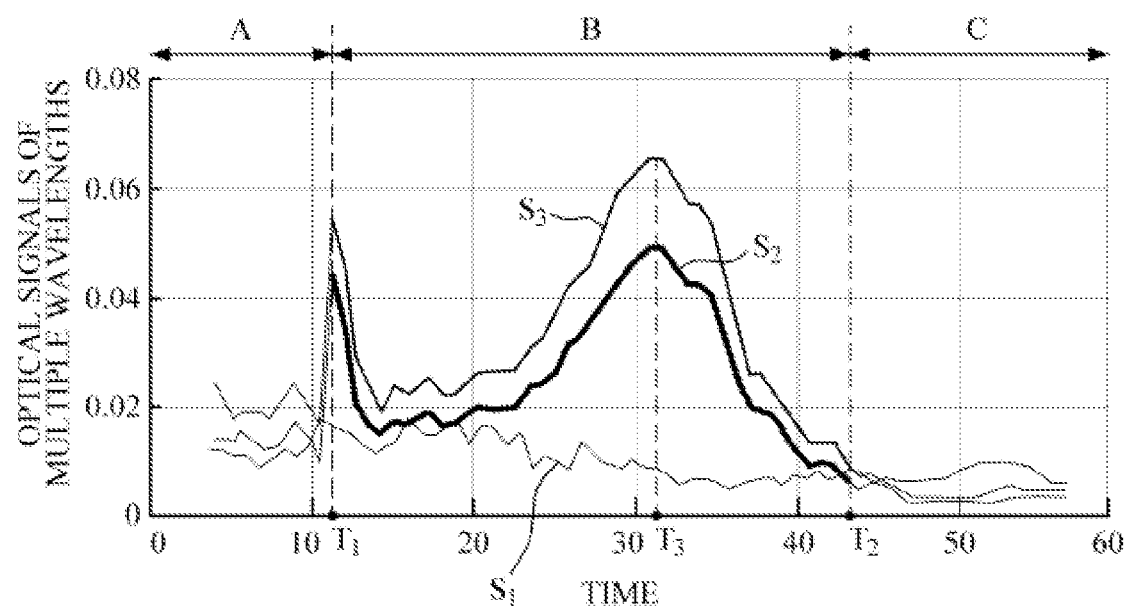
FIGS. 4A to 4D are diagrams for explaining a specific process of determining a suitable section for estimating oxygen saturation.

FIG. 4A is a graph illustrating normalized signals $S_1$, $S_2$, and $S_3$ obtained by normalizing an optical signal of a first wavelength, an optical signal of a second wavelength, and an optical signal of a third wavelength that are measured by the sensor part 110 over time. That is, as illustrated in FIG. 4A, the signal of each wavelength represents the magnitude of a pulse of a signal obtained by dividing an AC component signal of the optical signal of each wavelength by a DC component signal. In this case, the first wavelength $S_1$ is a shortest wavelength, the second wavelength $S_2$ is relatively longer than the first wavelength, and the third wavelength $S_3$ is relatively longer than the second wavelength. $T_3$ represents a point in time at which the normalized signal $S_2$ of the optical signal of the second wavelength and the normalized signal $S_3$ of the optical signal of the third wavelength reach the maximum signal intensity or the maximum amplitude.

Figure 4B:
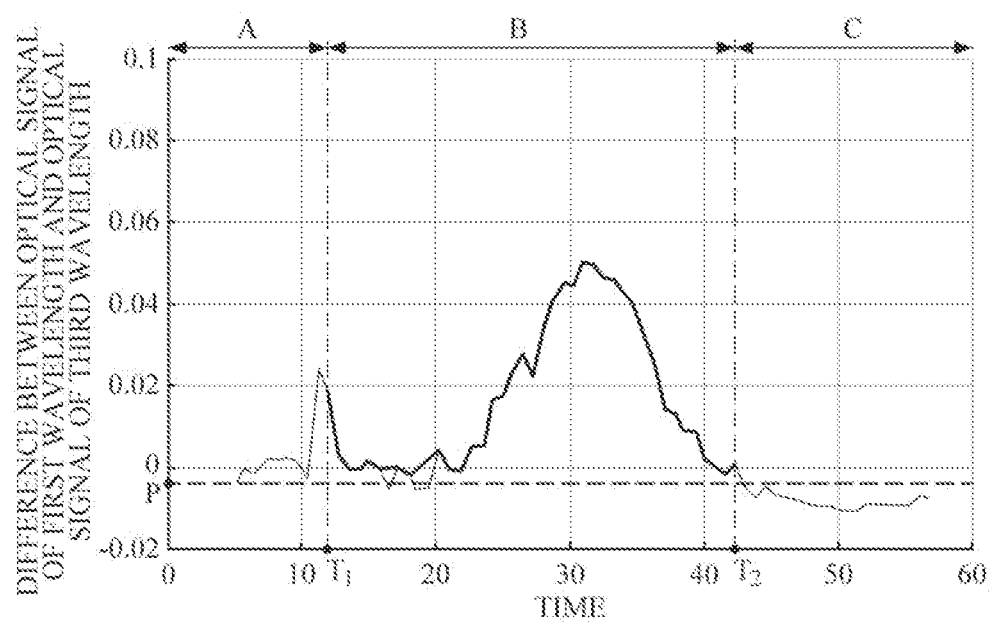

FIG. 4B is a graph showing a difference between signals of two wavelengths. When signals of three different wavelengths are measured as shown in FIG. 4A, the processor 120 may determine a suitable section by using a difference between the signal of the first wavelength that is the shortest wavelength and the signal of the third wavelength that is the longest wavelength.

In the graph of FIG. 4B, the difference between the optical signal of the first wavelength and the optical signal of the third wavelength is not significant in section A (0 to $T_1$). In section A, the blood vessel on the skin surface is not properly occluded due to a small force between the object and the sensor part (see section A in FIG. 4C), and therefore the optical signal of the third wavelength that is a relatively long wavelength and also the optical signal of the first wavelength that is the shortest wavelength are measured. In this section A (0 to $T_1$), external light is injected into the sensor part, and also venous oxygen saturation affects blood oxygen saturation to be measured, so that blood oxygen saturation fluctuates in a large range and has an unstable value (see section A of FIG. 4D).

In the graph of FIG. 4B, the difference between the optical signal of the first wavelength and the optical signal of the third wavelength in section B ($T_1$ to $T_2$) is relatively larger than that in section A. In section B, the force between the object and the sensor part is increased as compared to section A (see section B of FIG. 4C), and thus the blood vessel on the skin surface is first occluded so that the magnitude of the optical signal of the first wavelength that is the shortest wavelength decreases first. In this section B, oxygen saturation has a relatively stable value (see section B of FIG. 4D).

In addition, in the graph of FIG. 4B, the difference between the optical signal of the first wavelength and the optical signal of the third wavelength in section C ($T_2$ to end) is relatively small as compared to that in section B. In section C, the force between the object and the sensor part is increased as compared to that in section B (see section C of FIG. 4C), and hence the blood vessel deep in the skin is also occluded so that the magnitude of the optical signal of the third wavelength that is a relatively long wavelength also decreases. In this section C, the oxygen saturation fluctuates in a large range and has an unstable value (see section C of FIG. 4D).

In this way, section B may be determined as the relatively most suitable section for estimating oxygen saturation. Accordingly, a threshold P to determine section B as a suitable section may be preset, and the processor 120 may determine that section B in which the difference between the optical signal of the first wavelength and the optical signal of the third wavelength is greater than or equal to the threshold P is the suitable section. Here, the threshold P may be set differently according to each user.

Figure 4C:
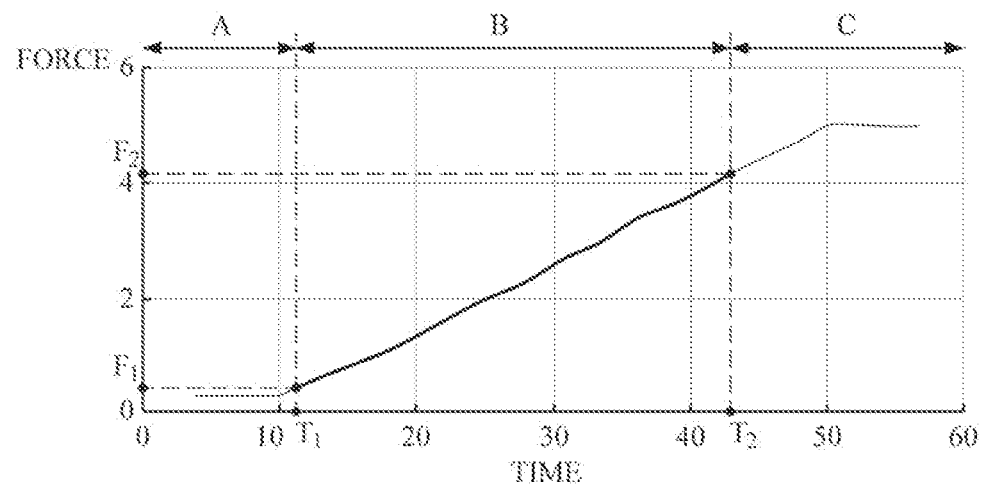

FIG. 4C is a graph showing the force between the object and the sensor part measured while the optical signal of the three wavelengths illustrated in FIG. 4A are measured.

As described above, if the force acting between the object and the sensor part is too low or too high, it is not suitable for estimating the user's oxygen saturation. Therefore, the suitable section for estimating oxygen saturation may be determined according to a threshold range of the force between the object and the sensor part.

FIG. 4C illustrates that the threshold range of the force between the object and the sensor part is set to $F_1$ to $F_2$, and thus section B in which the range of the force is measured as $F_1$ to $F_2$ may be determined as the relatively most suitable section for estimating oxygen saturation. In this case, the threshold range $F_1$ to $F_2$ of the force between the object and the sensor part may be different from one user to another according to the user's blood pressure, location of the blood vessel, and mechanical and optical properties of the skin, and the processor 120 may perform calibration to preset the threshold range of the force for each user for determining the suitable section for estimating oxygen saturation. For example, the processor 120 may obtain force values at predetermined points in time before and after the point at which the optical signal of the second wavelength or third wavelength measured by the multiple-wavelength optical signal measuring sensor 210 reaches the maximum amplitude, and may set the obtained force values as the minimum and maximum values of the threshold range of the force for determining the suitable section for estimating oxygen saturation.

Figure 4D:
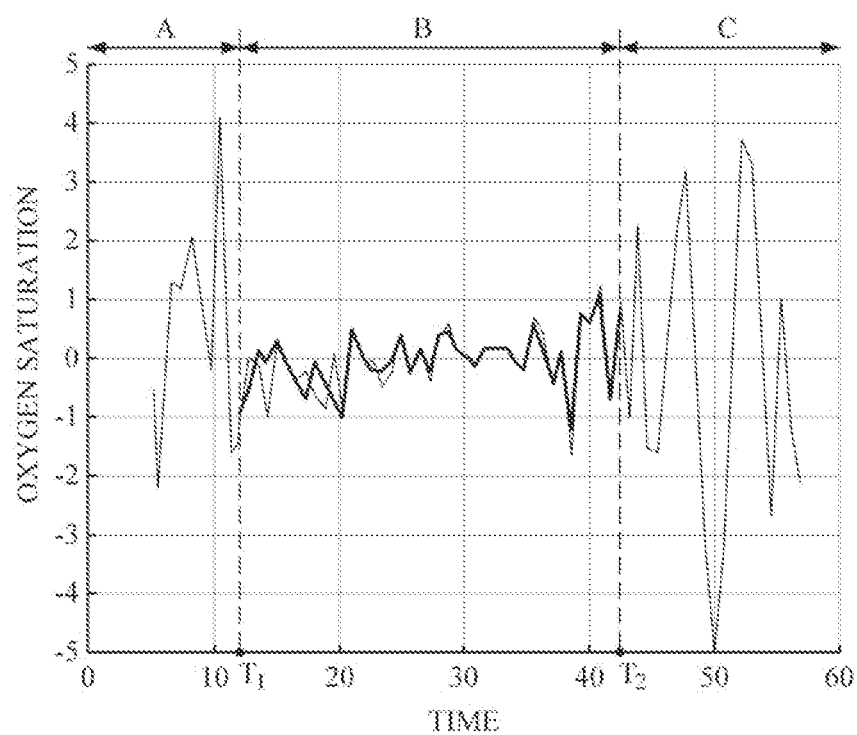

FIG. 4D is a graph showing the estimated oxygen saturation.

As described above, in section B ($T_1$ to $T_2$) in which the difference between the optical signal of the first wavelength and the optical signal of the third wavelength is greater than or equal to the threshold value P (see section B of FIG. 4B) and the force between the object and the sensor part falls within the threshold range $F_1$ to $F_2$ (See section B of FIG. 4C), the estimated oxygen saturation value does not fluctuate significantly and has a stable value.

Figure 5:
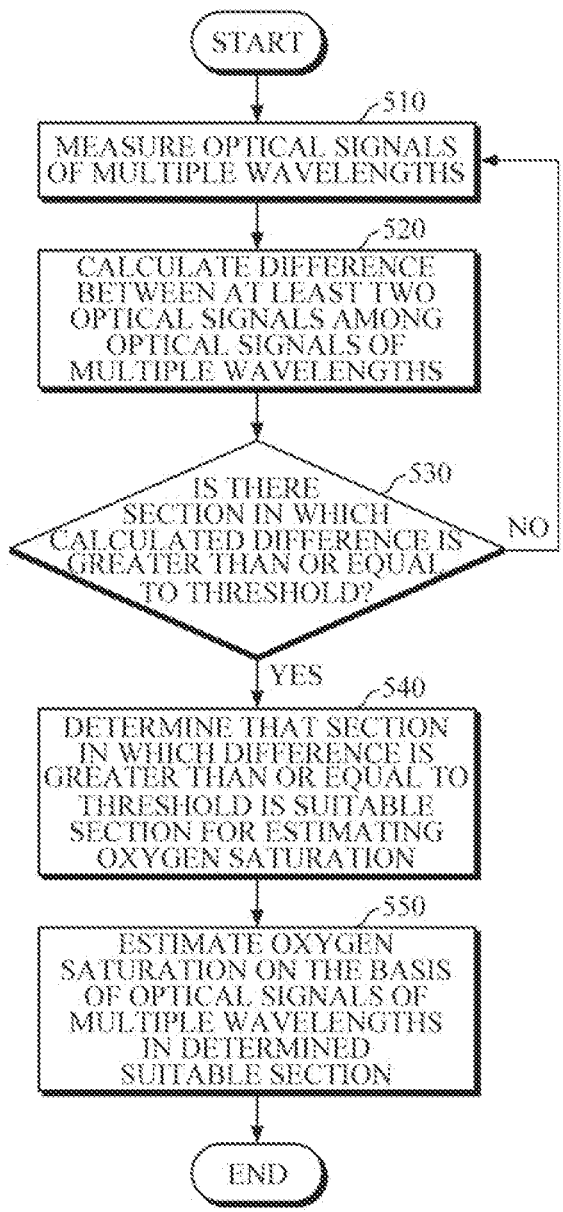
FIG. 5 is a flowchart illustrating a method of estimating oxygen saturation according to an exemplary embodiment.

FIG. 5 is a flowchart illustrating a method of estimating oxygen saturation according to an example embodiment.

First, optical signals of multiple wavelengths are measured (operation 510). In this case, the multiple wavelengths include a first wavelength that is a shortest wavelength, a second wavelength that is relatively longer than the first wavelength, and a third wavelength that is relatively longer than the second wavelength. Here, the first wavelength that is the shortest wavelength may be less than 640 nanometers.

Then, a difference between at least two optical signals among the optical signals of multiple wavelengths is calculated (operation 520). Here, the two optical signals may be the optical signal of the first wavelength and the optical signal of the second wavelength, or the optical signal of the first wavelength and the optical signal of the third wavelength.

Next, it may be determined whether there is a section in which the calculated difference is equal to or greater than a threshold (operation 530).

Then, if there is a section in which the difference is greater than or equal to the threshold, the section may be determined as a suitable section for estimating oxygen saturation (operation 540).

If there is no section in which the difference is greater than or equal to the threshold, a user may be requested to re-measure the optical signals of multiple wavelengths.

Next, oxygen saturation may be estimated based on the optical signals of multiple wavelengths in the determined suitable section (operation 550). At this time, a first feature value of the optical signal of the second wavelength and a second feature value of the optical signal of the third wavelength may be acquired and the oxygen saturation may be estimated based on the acquired first feature value and second feature value.

Figure 6:
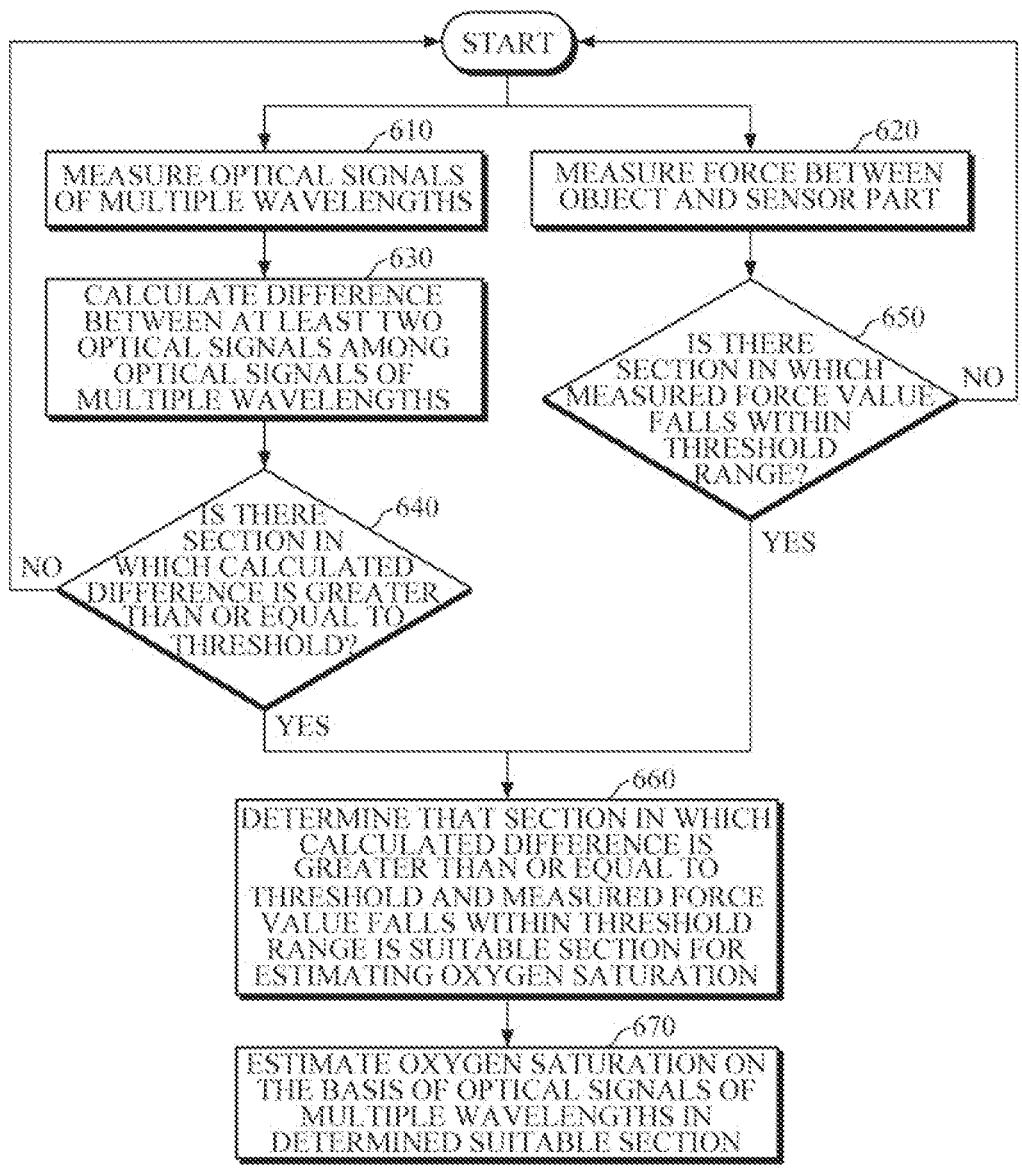
FIG. 6 is a flowchart illustrating a method of estimating oxygen saturation according to another example embodiment.

FIG. 6 is a flowchart illustrating a method of estimating oxygen saturation according to another example embodiment.

First, optical signals of multiple wavelengths may be measured (operation 610), and force between an object and a sensor part may be measured while the optical signals of multiple wavelengths are measured (operation 620).

Then, a difference between at least two optical signals among the optical signals of multiple wavelengths may be calculated (operation 630). In this case, a difference between the optical signals may be calculated using normalized signals obtained by normalizing each of the optical signals of multiple wavelengths. For example, the normalized signal may be a signal obtained by dividing an AC component of an optical signal of each wavelength by a DC component, but is not limited thereto.

Next, it may be determined whether there is a section in which the calculated difference is equal to or greater than a threshold value (operation 640). At this time, if there is no section in which the difference is greater than or equal to the threshold, a user may be requested to re-measure the optical signals of multiple wavelengths.

Next, it is determined whether there is a section in which the measured force value falls within a threshold range (operation 650). When it is determined that there is no section in which the measured force value falls within a threshold range, the user may be requested to re-measure the optical signals of multiple wavelengths.

Here, operations 630 to 650 are not limited to the illustrated order and may be performed in reverse order, in a different order, or in parallel.

Next, a section in which the calculated difference is greater than or equal to the threshold value and the measured force value falls within the threshold range may be determined as a suitable section for estimating oxygen saturation (operation 660).

Next, oxygen saturation may be estimated based on the optical signals of multiple wavelengths in the determined suitable section (operation 670).

Figure 7:
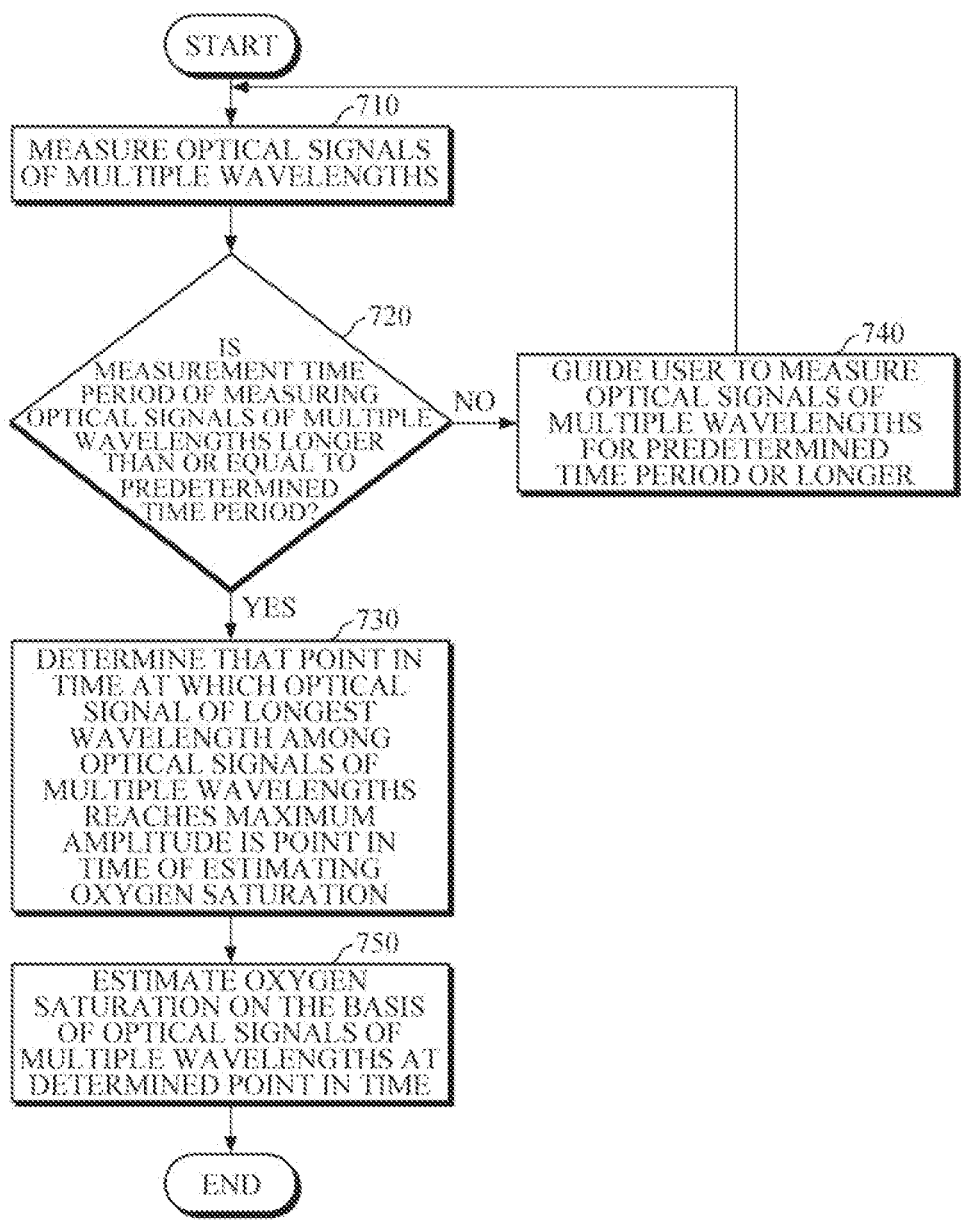
FIG. 7 is a flowchart illustrating a method of estimating oxygen saturation according to still another example embodiment.

FIG. 7 is a flowchart illustrating a method of estimating oxygen saturation according to still another example embodiment.

First, optical signal of multiple wavelengths are measured (operation 710).

Next, it may be determined whether the measurement time period of the optical signals of multiple wavelengths is longer than a predetermined time period (operation 720).

Next, when it is determined that the measurement time period is longer than or equal to the predetermined time period, a point at which the longest-wavelength optical signal among the optical signals of multiple wavelengths reaches the maximum amplitude may be determined as a point in time of estimating oxygen saturation (operation 730).

If the measurement time period is less than the predetermined time period, the user may be guided to measure the optical signals of multiple wavelengths for longer than the predetermined time period (operation 740).

Next, oxygen saturation may be estimated based on the optical signals of multiple wavelengths at the point in time determined in operation 730 (operation 750).

Figure 8:
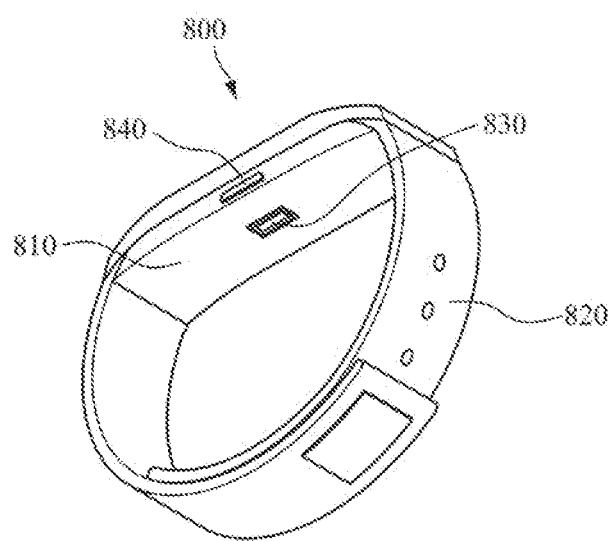
FIG. 8 is a diagram illustrating a wearable device according to an example embodiment.

Referring to FIG. 8, a wearable device 800 includes a main body 810 and a strap 820.

The strap 820 may be made of a flexible material. The strap 820 may be connected to opposite ends of the main body 810 and may wrap around the user's wrist such that the main body 810 is in close contact with an upper portion of the wrist. In this case, air may be injected into the strap 820 or an airbag may be included in the strap 820, so that the strap 820 may have elasticity according to a change in pressure applied to the wrist, and the change in pressure of the wrist may be transmitted to the main body 810.

A battery, which supplies power to the wearable device 800, may be embedded in the main body 810 or the strap 820. Further, a sensor part 830 may be mounted in a rear surface of the main body 810. The sensor part 830 may include one or more light sources and a detector. The sensor part 830 may include a multiple-wavelength optical signal measuring sensor and a force sensor. The multiple-wavelength optical signal measuring sensor may include a light source and a CMOS image sensor (CIS)-based image sensor. Further, the force sensor may include a pressure sensor, a combination of a pressure sensor and a contact area sensor, a pressure sensor array, etc.

A processor may be mounted in the main body 810 and may determine a suitable section for estimating oxygen saturation based on a difference between at least two optical signals among optical signals of multiple wavelengths measured by the sensor part 830. For example, the optical signals of multiple wavelengths may include an optical signal of a first wavelength that is a shortest wavelength, an optical signal of a second wavelength that is relatively longer than the first wavelength, and an optical signal of a third wavelength that is relatively longer than the second wavelength.

The processor may determine a suitable section for estimating oxygen saturation based on a difference between the optical signal of the first wavelength and the optical signal of the second wavelength, or a difference between the optical signal of the first wavelength and the optical signal of the third wavelength. The processor may normalize the measured optical signals of multiple wavelengths and calculate a difference between the optical signal of the first wavelength and the optical signal of the second wavelength, or a difference between the optical signal of the first wavelength and the optical signal of the third wavelength on the basis of the normalized signals. In this case, the processor may determine that a section in which the difference is greater than or equal to a threshold and/or measured force falls within a threshold range is the suitable section for estimating oxygen saturation.

In addition, the processor may acquire a first feature value of the optical signal of the second wavelength and a second feature value of the optical signal of the third wavelength at one point in time in the determined suitable section based on the normalized signals of the measured optical signals of multiple wavelengths, and estimate the oxygen saturation based on the acquired first feature value and second feature value. At this time, the processor may acquire the first feature value and the second feature value based on a point at which the optical signal of the second wavelength or the optical signal of the third wavelength reaches the maximum amplitude in the determined suitable section, or the median point in time of the determined suitable section, or may acquire the first feature value and the second feature value based on statistical values of the optical signal of the second wavelength and the optical signal of the third wavelength in the determined suitable section.

Based on receiving a request for estimating oxygen saturation from the user, the processor may guide the user for a force and/or pressure through a display and provide the user with an estimation result through the display when oxygen saturation is estimated. The display may be mounted on the front surface of the main body 810 to output the guide information and/or the result of estimation of oxygen saturation and receive the user's touch input and transmit the touch input to the processor.

In addition, a storage may be mounted inside the main body 810, and various criteria for estimating oxygen saturation and/or a processing result of the processor may be stored in the storage.

In addition, a manipulator 840 configured to receive a user's control command and transmit the control command to the processor may be mounted on the side of the main body 810, and the manipulator 840 may have a function for inputting a command to turn on/off the wearable device 800.

Further, a communication interface configured to transmit and receive data with the external device may be mounted in the main body 810. The communication interface may communicate with the external device, such as the user's smartphone, an oxygen saturation measuring device, or the like, to transmit and receive various types of data related to estimation of oxygen saturation.

Figure 9:
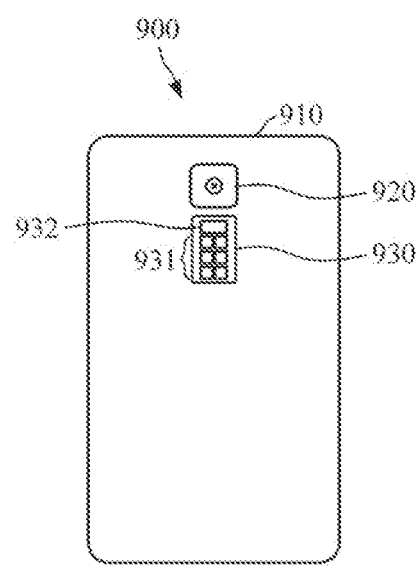
FIG. 9 is a diagram illustrating a smart device according to an example embodiment.

FIG. 9 is a diagram illustrating a smart device according to an example embodiment. The smart device 900 may include a smartphone, a tablet PC, etc. The smart device 900 may include the above-described various exemplary embodiments of the apparatuses 100, 200, and 300 for estimating oxygen saturation.

Referring to FIG. 9, the smart device 900 may have a sensor part 930 mounted on a rear surface of a main body 910. The sensor part 930 may include a light source 931 and a detector 932. The sensor part 930 may be mounted on the rear surface of the main body 910 as illustrated, but is not limited thereto. For example, the sensor part 930 may be formed on a fingerprint sensor on a front surface, a part of a touch panel, or a power button or volume button mounted on the side or an upper portion of the smart device. Also, the sensor part 930 may include a sensor configured to measure force between an object and the sensor part.

In addition, a display may be mounted on the front surface of the main body 910 to display various types of information, such as a result of estimation of oxygen saturation, a state in which the object is in contact with the sensor part, and guide information regarding force between the object and the sensor part.

An image sensor 920 may be mounted in the main body 910 as illustrated, and the image sensor 920 may capture an image of a finger when the user approaches the sensor part 930 to measure optical signals of multiple wavelengths and may transmit the image to the processor. In this case, the processor may identify a relative position of the finger relative to the actual position of the sensor part 930 and guide the user for information on the relative position of the finger through the display.

As described above, the processor may determine a suitable section for estimating oxygen saturation based on a difference between at least two optical signals among the measured optical signals of multiple wavelengths, and estimate oxygen saturation based on the optical signals of multiple wavelengths in the determined suitable section. A detailed description thereof will be omitted.

The example embodiments can be implemented by computer-readable code that is stored in a non-transitory computer-readable medium and that is executed by one or more processors. Code and code segments constituting the computer program can be inferred by a computer programmer skilled in the art. The computer-readable medium includes all types of record media in which computer-readable data are stored. Examples of the computer-readable medium include a ROM, a RAM, a CD-ROM, a magnetic tape, a floppy disk, and an optical data storage. Further, the record medium may be implemented in the form of a carrier wave such as Internet transmission. In addition, the computer-readable medium may be distributed to computer systems over a network, in which computer-readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating oxygen saturation, the apparatus comprising:
    a sensor configured to measure optical signals of multiple wavelengths by emitting multi-wavelength light onto an object, wherein the multi-wavelength light includes a first wavelength, a second wavelength that is longer than the first wavelength, and a third wavelength that is longer than the second wavelength; and
    a processor configured to:
    determine a section of the optical signals of the multiple wavelengths, in which a difference between a first optical signal of the first wavelength and a second optical signal of the second wavelength, or a difference between the first optical signal of the first wavelength and a third optical signal of the third wavelength is greater than or equal to a threshold;
    estimate oxygen saturation based on the optical signals of the multiple wavelengths, including the first wavelength, the second wavelength, and the third wavelength, in the section,
    wherein the processor is further configured to, based on there being no section in which the difference is greater than or equal to the threshold, provide information that requests a user to measure additional optical signals of the multiple wavelengths.

2. The apparatus of claim 1, wherein the first wavelength is less than 640 nanometers.

3. The apparatus of claim 1, wherein the sensor comprises a force sensor configured to measure a force between the object and the force sensor when the object is in contact with the force sensor, and
    wherein the processor is further configured to determine the section for estimating the oxygen saturation based on a value of the force measured by the force sensor.

4. The apparatus of claim 3, wherein the processor is further configured to determine a section in which the value of the measured force is within a threshold range as the section for estimating the oxygen saturation.

5. The apparatus of claim 4, wherein the processor is further configured to, based on there being no section in which the value of the measured force is within the threshold range, provide information that requests the user to measure the additional optical signals of the multiple wavelengths, or provide information that guides the user to apply a force within a reference range.

6. The apparatus of claim 3, wherein the processor is further configured to perform calibration to preset a threshold range of the force for the user.

7. The apparatus of claim 1, wherein the processor is further configured to acquire a first feature value of the second optical signal of the second wavelength and a second feature value of the third optical signal of the third wavelength in the section, and estimate the oxygen saturation based on the first feature value and the second feature value.

8. The apparatus of claim 7, wherein the processor is further configured to acquire the first feature value and the second feature value based on a point in time at which the second optical signal of the second wavelength or the third optical signal of the third wavelength includes a maximum amplitude in the section or a median point in time of the section, or acquire the first feature value and the second feature value based on statistical values of the second optical signal of the second wavelength and the third optical signal of the third wavelength in the section.

9. A method of estimating oxygen saturation, the method comprising:
    measuring optical signals of multiple wavelengths by emitting multi-wavelength light onto an object, wherein the multi-wavelength light includes a first wavelength, a second wavelength that is longer than the first wavelength, and a third wavelength that is longer than the second wavelength;
    determining a difference between at least two optical signals among the optical signals of the multiple wavelengths;
    determining a section of the optical signals of the multiple wavelengths, in which a difference between a first optical signal of the first wavelength and a second optical signal of the second wavelength, or a difference between the first optical signal of the first wavelength and a third optical signal of the third wavelength is greater than or equal to a threshold; and
    estimating oxygen saturation based on the optical signals of the multiple wavelengths, including the first wavelength, the second wavelength, and the third wavelength, in the section,
    wherein the method further comprises, based on there being no section in which the difference is greater than or equal to the threshold, providing information that requests a user to measure additional optical signals of the multiple wavelengths.

10. The method of claim 9, further comprising measuring a force between the object and a sensor when the object is in contact with the sensor, wherein the determining the section for estimating the oxygen saturation comprises determining the section based on a value of the measured force.

11. The method of claim 10, wherein the determining the section for estimating the oxygen saturation comprises determining a section in which the value of the measured force is within a threshold range as the section for estimating the oxygen saturation.

12. The method of claim 11, further comprising guiding the user to apply a force within a reference range based on there being no section in which the value of the measured force is within the threshold range.

* * * * *